US012784890B2

(12) United States Patent
Boas

(10) Patent No.: US 12,784,890 B2
(45) Date of Patent: Nov. 3, 2026

(54) SYSTEMS AND METHODS RELATED TO DOSIMETRY FOR RADIOEMBOLIZATION, CHEMOEMBOLIZATION, AND DRUG ELUTING EMBOLIZATION PROCEDURES

(71) Applicant: City of Hope, Duarte, CA (US)

(72) Inventor: Franz E. Boas, Duarte, CA (US)

(73) Assignee: City of Hope, Duarte, CA (US)

( * ) Notice: Subject to any disclaimer, the term of this patent is extended or adjusted under 35 U.S.C. 154(b) by 269 days.

(21) Appl. No.: 18/607,972

(22) Filed: Mar. 18, 2024

(65) Prior Publication Data

US 2024/0321427 A1 Sep. 26, 2024

Related U.S. Application Data

(60) Provisional application No. 63/491,165, filed on Mar. 20, 2023.

(51) Int. Cl.
*G16H 20/40* (2018.01)
*A61N 5/10* (2006.01)
*G16H 50/50* (2018.01)

(52) U.S. Cl.
CPC ........... *G16H 20/40* (2018.01); *A61N 5/1039* (2013.01); *G16H 50/50* (2018.01); *A61N 2005/1034* (2013.01)

(58) Field of Classification Search
CPC .......... A61N 5/1039; A61N 2005/1034; A61N 5/1001; A61N 5/1031; A61N 5/10; A61N 5/103; A61N 2005/109; A61N 5/1071; A61N 5/1043; A61N 5/1028; A61N 5/1075; A61N 2005/1087; G16H 20/40; G16H 50/50; G16H 40/60; G16H 10/60; A61B 6/58; A61B 6/542; A61B 6/037; A61B 6/032; G06F 30/25; G06T 2207/10081; G06N 5/01
USPC ........................................................ 378/65, 62
See application file for complete search history.

(56) References Cited

U.S. PATENT DOCUMENTS

2008/0049898 A1* 2/2008 Romesberg, III .... A61N 5/1031 378/65
2022/0241615 A1* 8/2022 Carabe-Fernandez ........................ G16H 50/50
2023/0191150 A1* 6/2023 Hirvonen ............. A61N 5/1031 378/65

OTHER PUBLICATIONS

Boas, F.E. et al. (Sep. 2017). "Radioembolization of Colorectal Liver Metastases: Indications, Technique, and Outcomes," *J Nucl Med* 58(9)(Suppl 2):104S-111S.
Boas, F.E. et al. (2020). "36—Embolotherapy for the Management of Liver Malignancies Other Than Hepatocellular Carcinoma," in Image-Guided Interventions (Third Edition) *Expert Radiology* 297-300.e1.

(Continued)

*Primary Examiner* — Irakli Kiknadze
(74) *Attorney, Agent, or Firm* — Mintz Levin Cohn Ferris Glovsky and Popeo, P.C.

(57) ABSTRACT

Systems and methods are configured to determine an effective local dose for a treatment procedure. The systems and methods are configured to determine a mean dose of a particle and a particle density at least a portion of tumor and at least a portion of normal tissue, perform a microdosimetry simulation or calculation, using the mean dose and the particle density, and determine the effective local dose, based on the microdosimetry simulation or calculation. A treatment plan can be arrived at pursuant to such systems and methods.

18 Claims, 7 Drawing Sheets

(56) References Cited

OTHER PUBLICATIONS

Braat, M.N. et al. (Feb. 2017). "Radioembolization-induced liver disease: a systematic review," *Eur J Gastroenterol Hepatol* 29(2):144-152.
Budczies, J. et al. (2012). "Cutoff Finder: a comprehensive and straightforward Web application enabling rapid biomarker cutoff optimization," *PLoS One* 7(12):e51862.
Core, J.M. et al. (Jun. 2020). "Increasing Yttrium-90 Dose Conformality Using Proximal Radioembolization Enabled by Distal Angiosomal Truncation for the Treatment of Hepatic Malignancy," *J Vasc Interv Radiol* 31(6):934-942.
Elschot, M. et al. (Feb. 2013). "Quantitative comparison of PET and Bremsstrahlung SPECT for imaging the in vivo yttrium-90 microsphere distribution after liver radioembolization," *PLoS One* 8(2):e55742.
Garin, E. et al. (Jan. 2021). "Personalised versus standard dosimetry approach of selective internal radiation therapy in patients with locally advanced hepatocellular carcinoma (DOSISPHERE-01): a randomised, multicentre, open-label phase 2 trial," *Lancet Gastroenterol Hepatol* 6(1):17-29.
Hermann, A.L. et al. (Sep. 2020, e-published Jun. 30, 2020). "Relationship of Tumor Radiation-absorbed Dose to Survival and Response in Hepatocellular Carcinoma Treated with Transarterial Radioembolization with $^{90}$Y in the Sarah Study," *Radiology* 296(3):673-684.
Horsman, M.R. et al. (Aug. 2016, e-published Mar. 16, 2016). "The impact of hypoxia and its modification of the outcome of radiotherapy," *J Radiat Res* 57(S1):i90-i98.
Nurili, F. et al. (Apr. 2021). "Transarterial Embolization of Liver Cancer in a Transgenic Pig Model," *J Vasc Interv Radiol* 32(4):510-517.e3.
Pasciak, A.S. et al. (May 2015). "The impact of an antireflux catheter on target volume particulate distribution in liver-directed embolotherapy: a pilot study," *J Vasc Interv Radiol* 26(5):660-669.
Pasciak, A.S. et al. (Apr. 2020, e-published Nov. 18, 2019). "The number of microspheres in Y90 radioembolization directly affects normal tissue radiation exposure," *Eur J Nucl Med Mol Imaging* 47(4):816-827.
Ridouani, F. et al. (Mar. 2021). "Relationship of radiation dose to efficacy of radioembolization of liver metastasis from breast cancer," *Eur J Radiol* 136:109539.
Spreafico, C. et al. (Apr. 2014). "The dosimetric importance of the number of 90Y microspheres in liver transarterial radioembolization (TARE)," *Eur J Nucl Med Mol Imaging* 41(4):634-638.
Stabin, M.G. et al. (Aug. 1994). "Bremsstrahlung radiation dose in yttrium-90 therapy applications," *J Nucl Med* 35(8):1377-1380.
Titano, J.J. et al. (2019). End-hole Versus Microvalve Infusion Catheters in Patients Undergoing Drug-Eluting Microspheres-TACE for Solitary Hepatocellular Carcinoma Tumors: A Retrospective Analysis, *Cardiovasc Intervent Radiol* 42(4):560-568.
Van Den Hoven, A.F. et al. (Jan. 2014). "The effect of intra-arterial angiotensin II on the hepatic tumor to non-tumor blood flow ratio for radioembolization: a systematic review," *PLoS One* 9(1):e86394.
Van Den Hoven, A.F. et al. (Jul. 2016). "Insights into the Dose-Response Relationship of Radioembolization with Resin 90Y-Microspheres: A Prospective Cohort Study in Patients with Colorectal Cancer Liver Metastases," *J Nucl Med* 57(7):1014-1019.
Walrand, S. et al. (Aug. 2014). "A hepatic dose-toxicity model opening the way toward individualized radioembolization planning," *J Nucl Med* 55(8):1317-1322.

* cited by examiner

SYSTEMS AND METHODS RELATED TO DOSIMETRY FOR RADIOEMBOLIZATION, CHEMOEMBOLIZATION, AND DRUG ELUTING EMBOLIZATION PROCEDURES

CROSS REFERENCE TO RELATED APPLICATIONS

This application claims priority to U.S. Provisional Patent Application No. 63/491,165 filed Mar. 20, 2023, entitled "SYSTEMS AND METHODS RELATED TO DOSIMETRY FOR RADIOEMBOLIZATION, CHEMOEMBOLIZATION, AND DRUG ELUTING EMBOLIZATION PROCEDURES" the contents of which is hereby incorporated by reference in its entirety and for all purposes.

BACKGROUND

Radioembolization is a method for treating diseased tissue such as liver tumors. Pursuant to an example radioembolization procedure involving a liver, particles comprising microspheres loaded with a radioisotope are delivered into a tumor-feeding artery to provide a dosage of radiation to the tumor. The resulting radiation dose in the tumor or liver (or in a portion of the tumor or liver) can be estimated using various methods, such as for example a post-procedure single-photon emission computed tomography (SPECT/CT) or positron emission tomography (PET/CT), or by using a partition model.

Such conventional methods unfortunately only provide a mean radiation dose over a given volume (such as a volume greater than 1 cubic centimeter.) Such methods consequently do not account for large variations in the local dose over a smaller length scale (such as less than 1 cm) due to random sized gaps between particles. Thus, the same mean radiation dose achieved via external beam radiation, radioembolization using a larger number of particles, and radioembolization using a smaller number of particles, do not have the same effects on the tumor or liver, resulting in unpredictable variations in tumor response and treatment toxicity.

SUMMARY

Disclosed are systems and methods configured for determining an effective local radiation dose for a treatment such as a radioembolization procedure. It should be appreciated that the systems and methods described herein are not limited to a particular procedure (such as radioembolization procedure) and can be used with other procedures such as chemoembolization and drug eluting embolization procedures in non-limiting examples.

The disclosed systems and methods account for a quantity of treatment particles delivered into a given tissue volume and further account for any gaps between such particles. The disclosed systems and methods enable a user to prescribe an optimal or improved number of particles as well as an optimal or improved activity per particle. This advantageously permits a therapeutic tumor dose while also reducing injury to normal (i.e., non-diseased) tissue.

The disclosed systems and methods are configured to determine an effective local dose for radioembolization, chemoembolization, or drug-eluting embolization procedures. The systems and methods account for one or more factors including the number of particles delivered, and the gaps between particles. This enables a user, such as a physician, to prescribe an optimal number (or otherwise improved number relative to conventional methods) of particles, and an optimal or improved amount of radiation or drug per particle, such as to achieve a therapeutic tumor dose, while possibly reducing injury to normal tissue. In a non-limiting example, the particles are glass microspheres or resin microspheres.

In an example system and method, a mean dose and particle density in both the tumor and normal tissue are determined using a partition model, or particle flow model, such as by using a computer processor system. Next, the computer processor system performs microdosimetry simulations to estimate dose heterogeneity within the tumor and/or normal tissue, accounting for the local particle density, and to calculate an effective local dose. In an embodiment, the microdosimetry is a Monte Carlo simulation. The computer processor system then adjusts a quantity of particles delivered, and the amount of radioactivity or drug per particle, to increase or maximize the effective dose to tumor, and reduce or minimize the effective dose to normal tissues. The computer processor system and/or a user can treat a patient and/or formulate or adjust a treatment plan for a patient.

In one aspect, there is disclosed a method of determining an effective local dose for a treatment procedure, comprising: determining a mean dose of a particle and a particle density at least a portion of tumor and at least a portion of normal tissue; performing a microdosimetry simulation or calculation, using the mean dose and the particle density; and determining the effective local dose, based on the microdosimetry simulation or calculation.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

These and other features will be more readily understood from the following detailed description taken in conjunction with the accompanying drawings, in which.

It is noted that the drawings are not necessarily to scale. The drawings are intended to depict only typical aspects of the subject matter disclosed herein, and therefore should not be considered as limiting the scope of the disclosure.

DETAILED DESCRIPTION

Embodiments of systems and methods for determining an effective local dose for a treatment such as a radioembolization procedure or other procedures. The systems and methods are configured for treating a target tissue of a patient, forming a treatment plan for a patient, and/or modifying a treatment plan.

Figure 1:
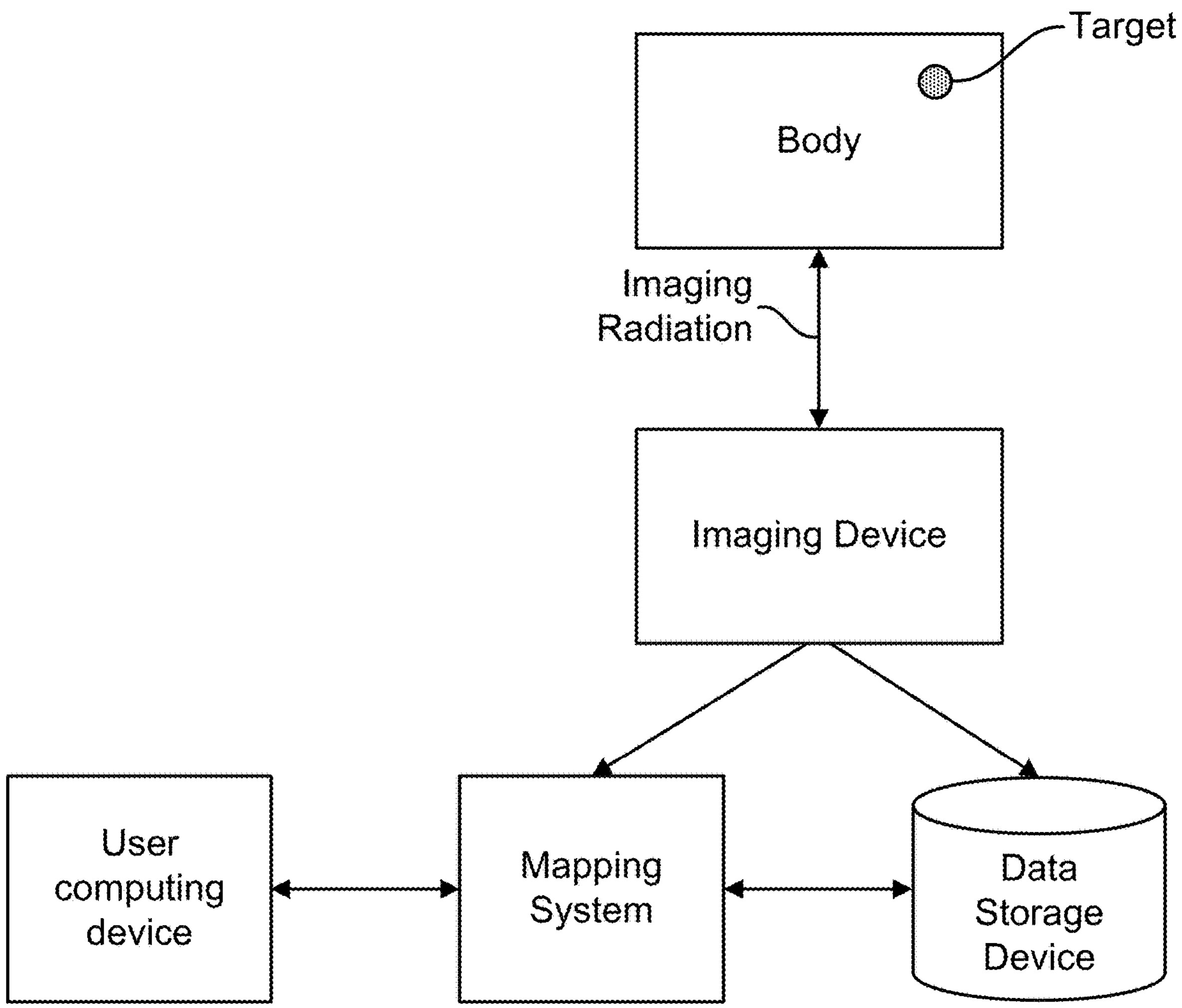
FIG. 1 is a diagram illustrating one exemplary embodiment of an operating environment including a system configured to determine an effective local dose and to treat a patient.

FIG. 1 is a schematic diagram illustrating an embodiment of an operating environment including an imaging device (such as a scanner), a mapping system configured to map data to an image, a data storage device, and a user computing device including a display device. The operating environment may also include one or more devices configured to form an image on a medium, such as a printer that prints images on paper. As shown, the imaging device, data storage device, mapping system, and user computing device can be in communication with one another and/or other devices/systems (e.g., via a network).

The imaging device can be configured to acquire one or a plurality of images of a tissue region such a tissue region that contains a tumor. The system is sometimes described herein in a non-limiting example of the tissue region being a liver although the tissue region can vary. In general, the imaging device can include at least one sensor configured to detect an imaging radiation (e.g., reflected from or transmitted through the target). In certain embodiments, the imaging device can include an emitter configured to emit the imaging radiation. In other embodiments, the emitter can be housed separately from the imaging device. Examples of the imaging device can adopt a variety of configurations. Non-limiting examples of the imaging device can include a magnetic resonance imaging (MRI) device, a positron emission tomography (PET) device, a computerized tomography (CT) device, a fluoroscopy device, an ultrasound device, or a single photon emission computed tomography (SPECT) device.

Figure 2:
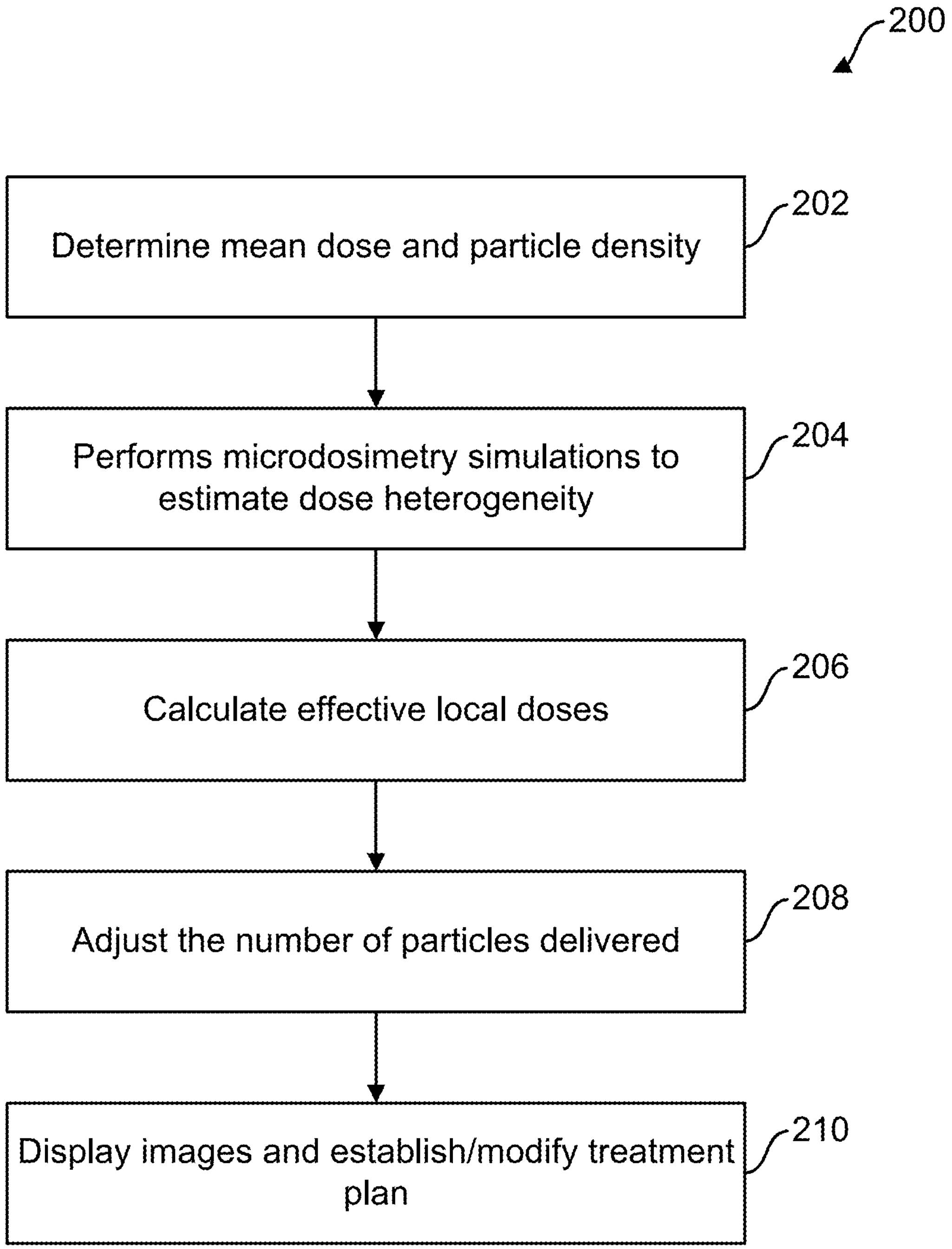
FIG. 2 is a diagram illustrating an embodiment of a general method for calculating an effective dose for radioembolization of tissue.

An embodiment of a method 200 for calculating an effective dose for radioembolization of tissue is illustrated in FIG. 2. As mentioned, radioembolization is a non-limiting example and the disclosed methods and systems can be used with other treatment procedures including for example chemoembolization and drug-eluting embolization procedures. The method 200 includes operations 202-210. Embodiments of the method can be implemented by one or more computer processors of the system and may include greater or fewer operations than illustrated in FIG. 2 and the operations can be performed in an order different than that illustrated in FIG. 2. In addition, one or more operations of the system can optionally performed using interaction of a human.

In operation 202, the system determines a mean dose of treatment particles and particle density in the tumor, portion of the tumor, and/or normal tissue. This is performed using a partition model, particle flow model, or other process. A "local dose" refers to the dose of particles in a specific target volume, such as a tumor, portion of a tumor, or normal tissue. The "local dose" can also refer to the dose of particles at a point within the target volume. Pursuant to operation 202, the system (in a non-limiting example) measures tumor-to-normal (T:N) ratio on $^{99m}$Tc-MAA SPECT/CT (such as with attenuation correction). This can be performed using one or more predetermined regions of interest relative to a region of target tumors. The regions of interest can also be defined over the surrounding normal liver tissue such as within the treated arterial distribution. A tumor particle density (particles/cm$^3$) is calculated, based on the number of particles delivered, tumor-to-normal ratio, tumor volume, and liver volume. A tumor dose (Gy) is related to the delivered activity, tumor-to-normal ratio, tumor volume, and liver volume.

In a non-limiting example, the particles are glass microspheres or resin microspheres.

With respect to a partition model, the particles injected into the tumor are partitioned among multiple regions of compartments of the target tissue, such as a tumor and liver compartment. Using a partition model, the mean particle density in the tumor is represented as follows:

$$d = \frac{p}{v_t + \frac{v_l}{r}}$$

where:

d=particle density in tumor (particles/cm$^3$)

p=number of particles delivered to the liver (after correcting for lung-shunt fraction)

$v_t$=tumor volume (cm$^3$)

$v_l$=liver volume (excluding tumor, cm$^3$); and r=T:N ratio on $^{99m}$Tc-MAA SPECT/CT The system alternately measures particle density or dose in predetermined portion of the tumor, such as voxel or other, predetermined portion of the tumor, rather than the entire tumor. A similar calculation can be performed for chemoembolization or drug-eluting embolization procedures, where the local drug dose is measured in mcg/cm$^3$ (for example) rather than Gy.

The tumor-to-normal ratio can change over the course of an embolization procedure. Particle flow to tumor and liver can be simulated using a physical model. In an example embodiment described with reference to FIG. 3, the physical model is described in a context of vascular resistance and capacitance (for receiving embolic particles). Particles initially flow towards low resistance arteries. The particles then shift towards high capacitance arteries as embolization approaches stasis.

Figure 3:
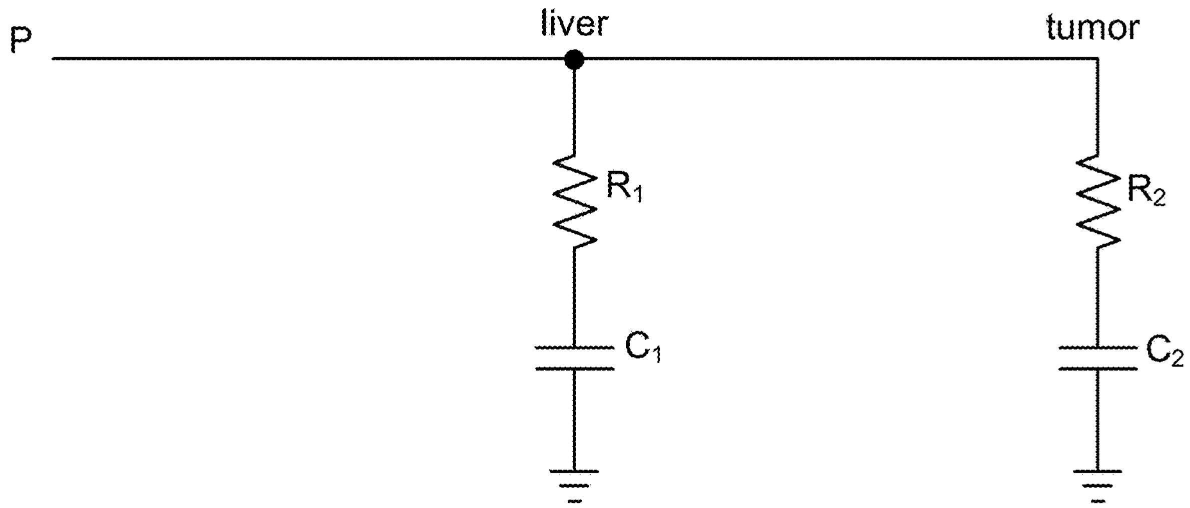
FIG. 3 is a schematic representation of a physical model in a context of vascular resistance and capacitance.

In the example model of FIG. 3, $$Q_1(t) = C_1 P\left(1 - e^{-t/R_1C_1}\right)$$

$$Q_2(t) = C_2 P\left(1 - e^{-t/R_2C_2}\right)$$

Thus, the initial T:N ratio (t=0) depends on the ratio of the resistances, and the final T:N ratio (after embolizing to stasis, t=∞) depends on the ratio of the capacitances. This is one reason that the T:N ratio changes during embolization. Low resistance tumors can be targeted with low particle density radioembolization, and high capacitance tumors can be targeted with high particle density radioembolization.

Figure 4B:
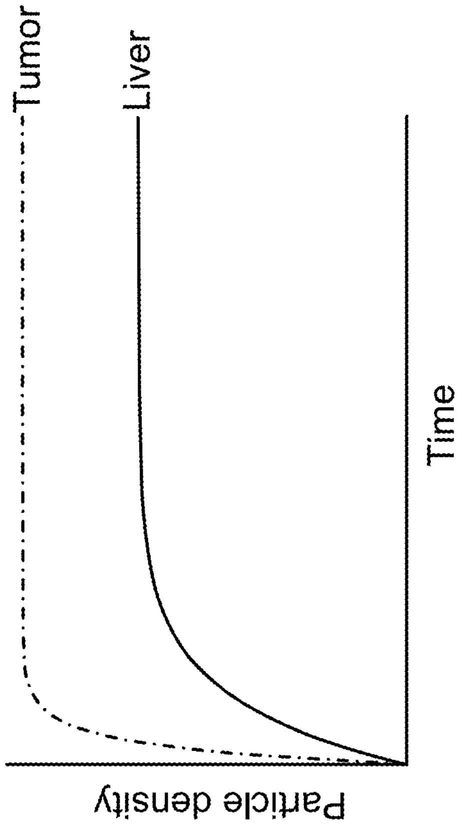
FIG. 4B shows a particle density over time for a low resistance tumor.
Figure 4A:
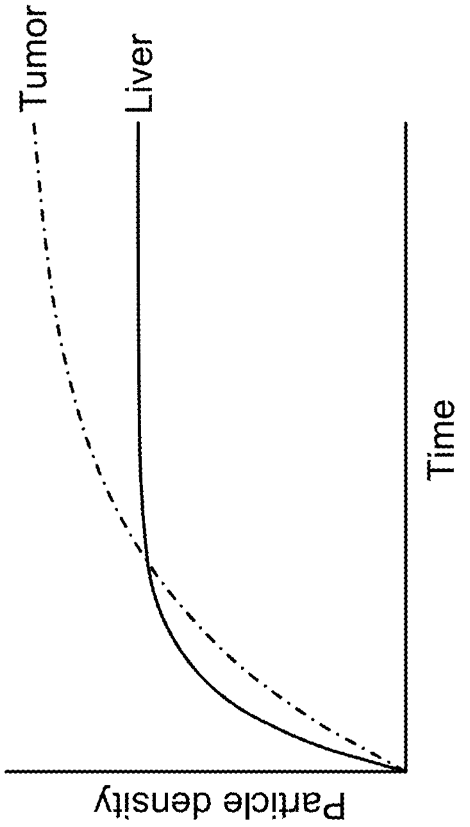
FIG. 4A shows a chart of particle density over time for a tumor having high resistance and high capacitance characteristics.

FIG. 4A shows a chart of particle density over time for a tumor having high resistance and high capacitance characteristics, which is characterized as a hypovascular tumor. In the example of FIG. 4A, the initial T:N ratio is 0.5. As embolization approaches stasis, the particles flow only to the tumor and a final T:N ratio approaches 1.4. FIG. 4B shows a particle density over time for a low resistance tumor, characterized as a hypervascular tumor. The T:N ratio is highest during initial embolization. The initial T:N ratio is 5. As embolization approaches stasis, particles only flow to the liver (rather than the tumor) and the final T:N ratio is 1.4.

Tumor-to-normal ratio can also be estimated from imaging, pathology, or clinical information. For example, it can be estimated based on enhancement on CT, enhancement on MRI, doppler ultrasound, enhancement on angiography, flow rate on angiography, PET/CT or SPECT/CT after radiotracer injection into the tumor-feeding artery, or CT showing retained contrast or radiopaque beads after embolization.

With reference again to the flow diagram of FIG. 2, in operation 204 the system next performs one or more microdosimetry simulations to estimate dose heterogeneity within the target tissue region, which as mentioned can be the tumor, a portion of the tumor, or normal tissue. A continuous function can be fit to the microdosimetry simulations. In operation 206, the system calculates effective local doses for the target tissue region. "Effective dose" or "Effective local dose" refers to any dose measurement (such as median dose, $1^{st}$ percentile dose, or percentage of the target volume that receives more than a target dose) that provides information beyond a traditional mean dose measurement. In the microdosimetry simulations, particles are distributed within the target volume, and the dose at each point within the target volume is determined by calculating the distance from the point to each particle and adding up the dose contribution from each particle. The dose distribution (fraction of the target volume that sees a given dose) can be summarized into an effective dose, by calculating percentiles, or by calculating the percentage of the volume that sees more than the target dose.

Given the mean dose (Gy) and particle density (particles/$cm^3$), microdosimetry simulations are performed to calculate microdosimetry maps, dose distributions, median doses, and $1^{st}$ percentile doses. First, activity per particle is calculated using the standard 50 Gy kg/GBq conversion factor (for $^{90}Y$). Second, an average of particles per cluster is assumed (such as 5 particles per cluster) and clusters are distributed in 3D space following a uniform random distribution. Finally, for each point in the 3D volume, the dose is calculated by summing up the dose from each cluster, using data on the dose as a function of distance from a point source of $^{90}Y$.

Doses calculated from SPECT/CT are mean doses over a volume larger than about 1 $cm^3$. On the other hand, microdosimetry simulations provide information on dose heterogeneity on a microscopic scale (down to resolution of individual microspheres), due to random gaps between particles.

Figure 5A:
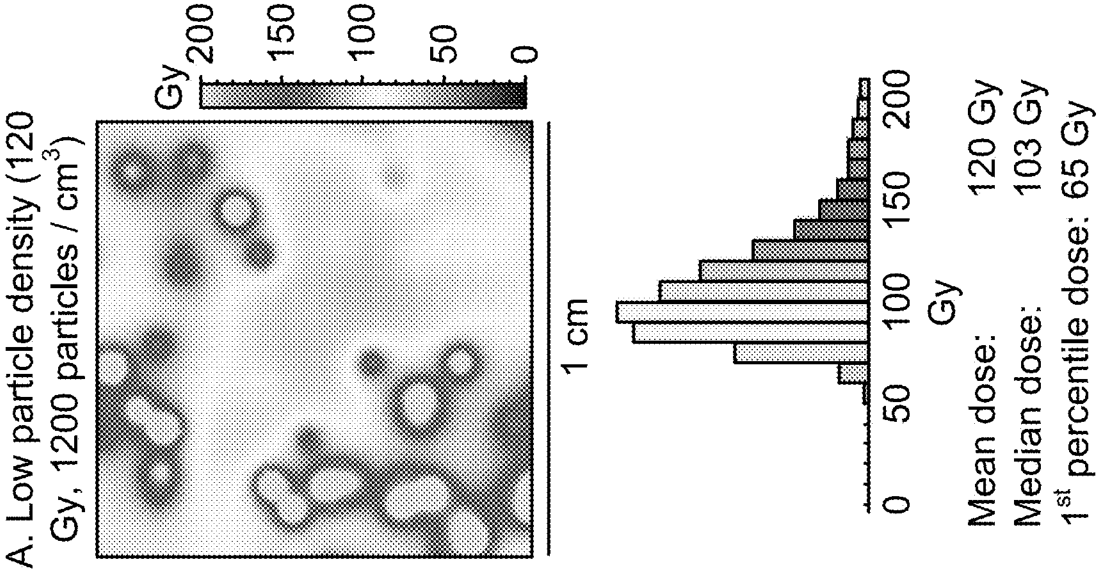
FIGS. 5A-5D are example microdosimetry maps showing mean dose and dose-volume histograms.
Figure 5B:
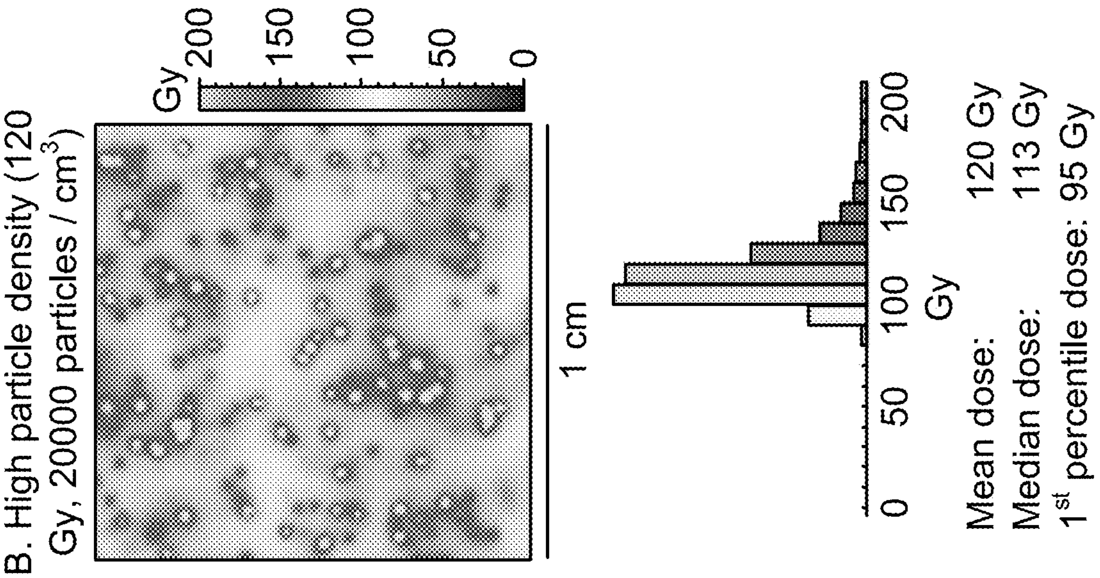
Figure 5C:
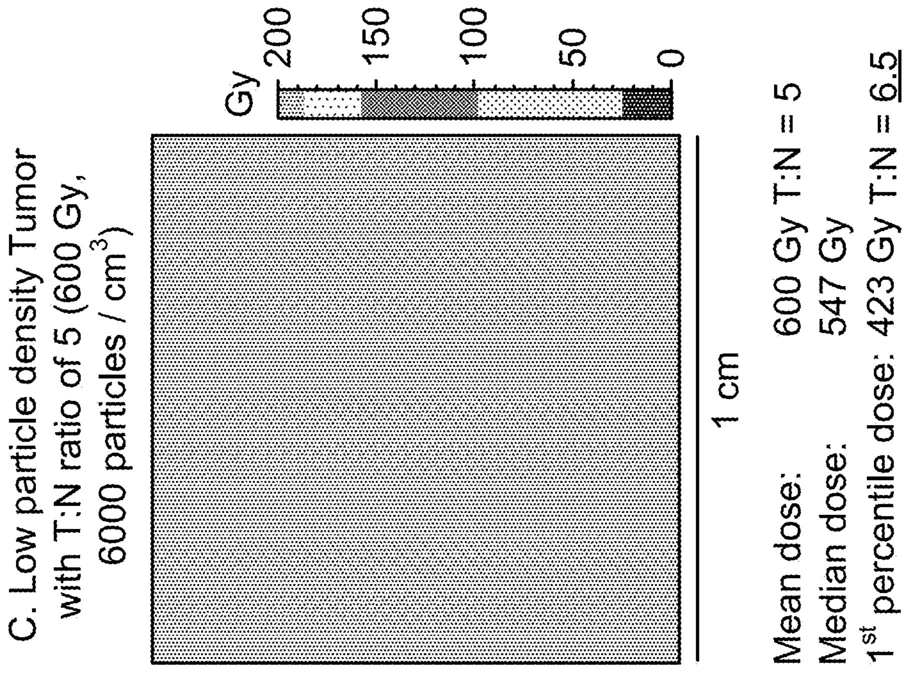
Figure 5D:
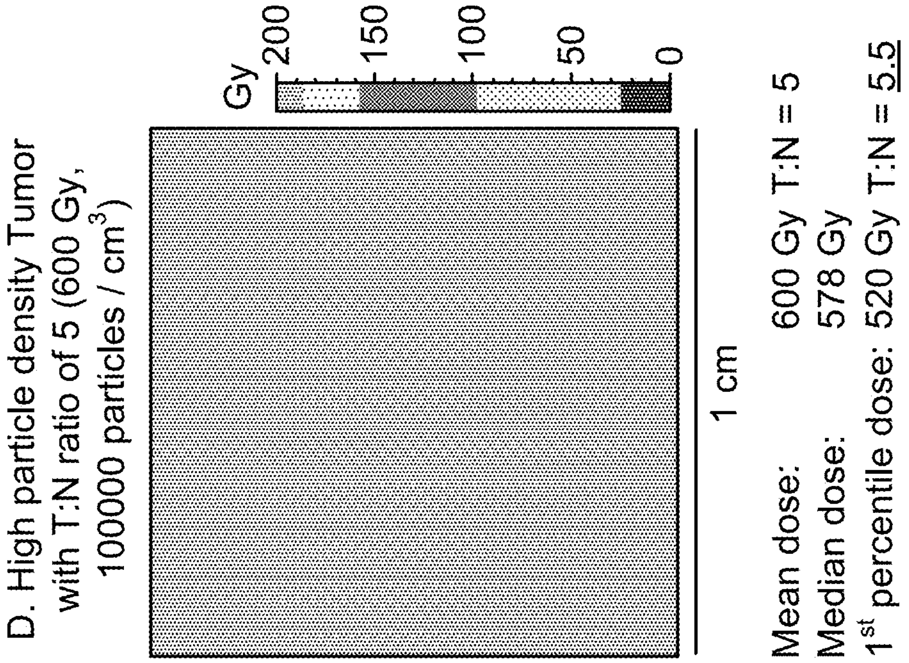

FIGS. 5A-5D are example microdosimetry maps showing mean dose (Gy), point doses, and dose volume histograms. FIG. 5A shows low particle density while FIG. 5B shows a high particle density. Although the mean dose is the same in both FIGS. 5A and 5B, the dose distribution differs between the two maps. With low particle density, cold spots are present between particles. FIGS. 5C and 5D show corresponding microdosimetry heat maps and does in a homogenous hypervascular tumor with a T:N ratio of 5, which corresponds to 5 times the mean dose and 5 times the density. In this example, for both low particle density and high particle density, the dose is uniform throughout the tumors.

FIGS. 5A-5D demonstrate that the mean dose (Gy) in the liver or tumor can be misleading: the dose can be much higher immediately next to a $^{90}Y$ microsphere, and much lower in the gaps between microspheres. The $1^{st}$ percentile dose provides an estimate of the "minimum" dose in the gaps between particles (99% of the volume receives more than the $1^{st}$ percentile dose).

High particle density results in a more uniform dose distribution, with smaller hot spots as well as smaller cold spots (FIG. 5A vs FIG. 5B). Cold spots are presumably helpful when they occur in normal liver, but harmful when they occur in the tumor. The difference in $1^{st}$ percentile dose could explain why 120 Gy glass, 120 Gy resin, and 120 Gy external beam radiation are not equivalent. The $1^{st}$ percentile dose accounts for the effects of particle density, and thus allows us to compare glass and resin $^{90}Y$ doses on the same scale.

Low particle density appears to be helpful for hypervascular tumors (better $1^{st}$ percentile T:N ratio), because the tumor dose is uniformly therapeutic, while the normal liver is protected by cold spots. In a hypovascular tumor, the situation is reversed, because low particle density translates into cold spots in the tumor.

Figure 6:
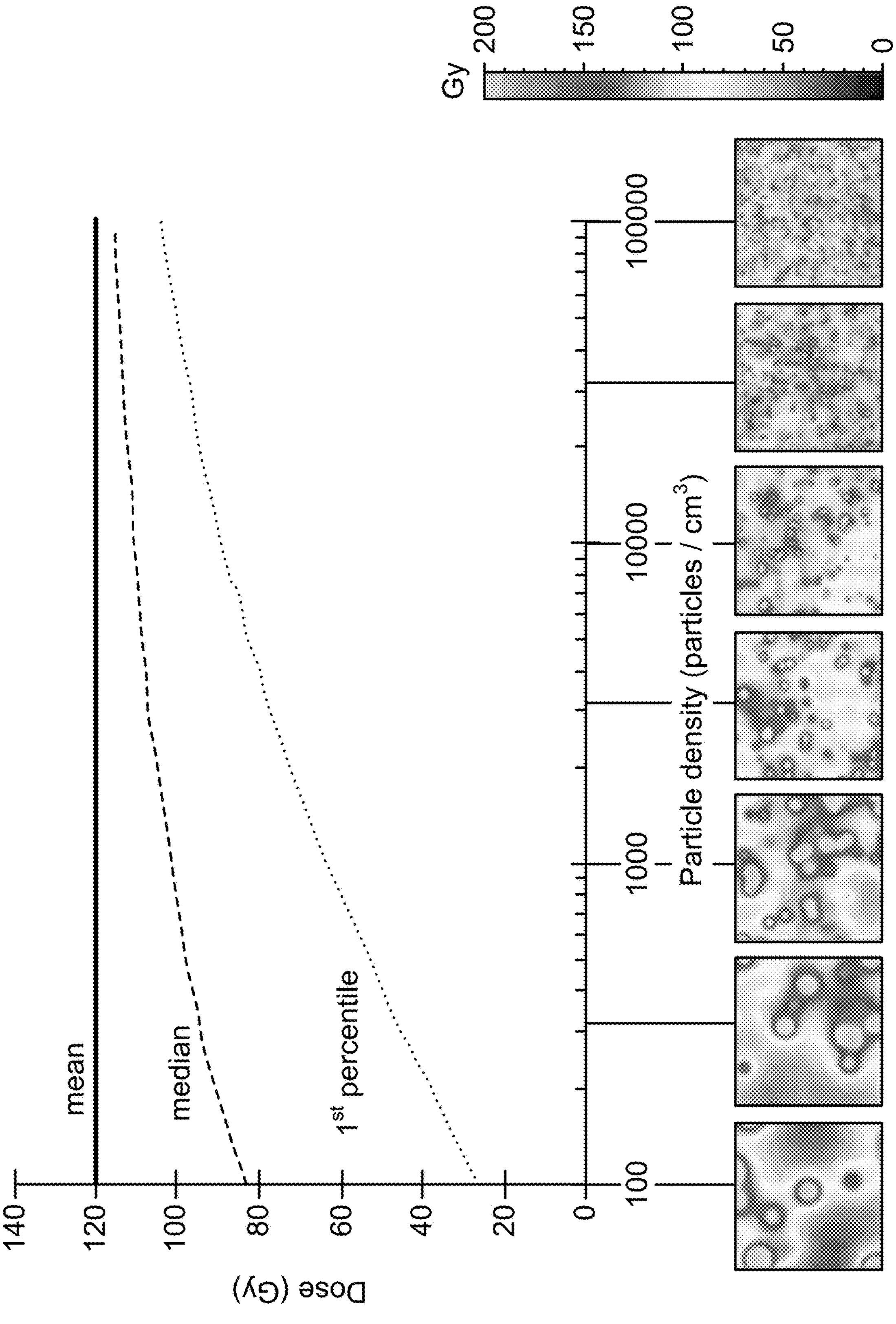
FIG. 6 shows a relationship between mean, median, and $1^{st}$ percentile dose, as a function of particle density, based on microdosimetry simulations.

The relationship between mean, median, and $1^{st}$ percentile dose, as a function of particle density, is shown in FIG. 6. The $1^{st}$ percentile dose decreases when the particle density is decreased, due to random gaps between particles.

Mean doses can be converted into median or $1^{st}$ percentile doses, using the curves in FIG. 6. Alternatively, the $1^{st}$ percentile dose can be estimated using the following formula:

$$g\left(1+\frac{a}{d}+\frac{b}{\sqrt[3]{d}}\right)^{-c}t$$

$$g\left(1+\frac{3.48}{d}+\frac{0.876}{\sqrt[3]{d}}\right)^{-7.41},$$

where g is the mean dose (Gy), and d is the particle density (particles/$cm^3$). a, b, and c are constants. In a non-limiting example embodiment shown above, a=3.48, b=0.876 and c=7.41. In another non-limiting example embodiment, a=36.5, b=3.42 and c=2.

The aforementioned formula was fit to the curves in FIG. 6. The formula provides a maximum error of <1%, in the range $100 \le d \le 100000$. It has the correct asymptotic behavior: the $1^{st}$ percentile dose is 0 when the particle density is 0, and the $1^{st}$ percentile dose equals the mean dose when the particle density is infinite. Note that the effective particle density can be scaled to account for a greater or lesser degree of particle clustering. In particular, the effective particle density can be scaled, in order to match clinical data on doses required to cause tumor necrosis.

In an alternate embodiment, rather than distributing particles using a uniform random distribution, particles can be placed into the volume in a clustered fashion. New particles can be preferentially placed near existing particles. Heterogeneous tumors can be modeled by assuming that a portion of the tumor only sees a fraction of the average particle density. Particles can be placed within a branching arterial tree. For a uniform random distribution of particles, the number of particles in a voxel follows the Poisson distribution; but other probability density functions could be used to account for tumor heterogeneity.

In another alternate embodiment, rather than performing the full microdosimetry simulation, gaps can be estimated using statistical methods. For example, if particles are randomly distributed, with d particles/$cm^3$, then the distance s (in cm) from a point in the liver to the closest microsphere follows a Weibull distribution, with probability density function $4\pi ds^2 e^{-4\pi ds^3/3}$. The distance to the closest microsphere can then be converted to the expected local dose. Or rather than examining the $1^{st}$ percentile dose, the fraction of the volume that receives greater than the target dose can be calculated.

In operation 208, the system adjusts the number of particles delivered, and the amount of radioactivity or drug per particle, to increase or maximize the effective dose to the tumor, and to decrease or minimize the effective dose to normal tissues, or both.

There are several possible criteria that can be used to determine the optimal number of particles, and optimal amount of radioactivity or drug per particle. Such criteria may include one or more of the following non-limiting examples:

Maximize $1^{st}$ percentile (or another percentile) tumor dose, while keeping liver dose below a threshold value.

Maximize percentage of tumor that receives a therapeutic dose, while keeping the percentage of liver that receives a toxic dose below a threshold value.

Minimize $1^{st}$ percentile (or another percentile) liver dose, while keeping tumor dose above a threshold value.

Maximize the ratio of $1^{st}$ percentile (or another percentile) tumor dose to liver dose.

Maximize the ratio of percentage of tumor that receives a therapeutic dose, to percentage of liver that receives a toxic dose.

The criteria can further include combinations of one or more of the above criteria.

In a non-limiting example, radioembolization can be performed using particles containing $^{90}Y$, $^{166}Ho$, or other radioisotopes. Chemoembolization can be performed using particles loaded with cytotoxic chemotherapy. Drug-eluting embolization can be performed using particles containing targeted therapies, antibodies, immunotherapy agents (including checkpoint inhibitors, vaccine adjuvants, immune stimulants, viruses, polymers, and cell therapies), or other drugs. These procedures can be used to treat tumors in the liver, kidney, lungs, pancreas, prostate, or other organs. For chemoembolization or drug-eluting embolization procedures, local drug dose is measured in meg/cm$^3$ rather than Gy. Point doses are calculated using data on the drug concentration as a function of distance from a drug-eluting bead.

With reference again to the flow diagram of operation 210, one or more resulting images and/or data are displayed on a computing device. Such images or data can also be recorded or displayed on a medium, such as by printing on paper for example. The images and/or data can also be used to establish and/or modify a treatment plan for the patient or subject such as in response to the steps described herein. The subject may also be treated pursuant to such a treatment plan.

Certain exemplary embodiments have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in analog electronic circuitry, digital electronic circuitry, and/or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web browser through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

The invention claimed is:

1. A method of determining an effective local dose for a treatment procedure, comprising:

determining a mean dose of a particle and a particle density at least a portion of tumor and at least a portion of normal tissue;

performing a microdosimetry simulation or calculation, using the mean dose and the particle density;

determining the effective local dose, based on the microdosimetry simulation or calculation; and determining the mean dose and the particle density via a partition model.

2. The method of claim 1, wherein the microdosimetry simulation comprises a Monte Carlo simulation.

3. The method of claim 1, further comprising treating a patient pursuant to the effective local dose.

4. The method of claim 1, further comprising preparing a treatment plan for a patient pursuant to the effective local dose.

5. The method of claim 1, wherein the effective dose is the dose at which a given fraction of the target volume receives less than the effective dose.

6. The method of claim 1, wherein the effective dose is a volume percentage of the target volume that receives more than the target dose.

7. The method of claim 1, wherein a continuous function is used to approximate the microdosimetry simulations.

8. The method of claim 7, further comprising using a formula $$g\left(1+\frac{a}{d}+\frac{b}{\sqrt[3]{d}}\right)^{-c}$$

to calculate the effective local dose, where g is a mean dose, d is a particle density, and wherein a=36.5, b=3.42 and c=2.

9. The method of claim 1, wherein a tumor-to-normal ratio is estimated based on at least one of enhancement on CT, enhancement on MRI, doppler ultrasound, enhancement on angiography, flow rate on angiography, PET/CT or SPECT/CT after radiotracer injection into the tumor-feeding artery, or CT showing retained contrast or radiopaque beads after embolization.

10. The method of claim 1, wherein the tumor-to-normal ratio is estimated based on a particle flow model, wherein the particle flow model includes both vascular resistance and capacitance for receiving embolic particles.

11. The method of claim 1, wherein at least one of the amount of radiation or drug, and/or the number of particles administered to a patient is adjusted to achieve a minimum tumor effective dose, maximum non-tumor effective dose, or both.

12. The method of claim 1, wherein the number of particles delivered is adjusted to maximize the tumor effective dose, divided by the non-tumor effective dose.

13. The method of claim 1, wherein the tumor is in the liver, lung, kidney, pancreas, or prostate.

14. The method of claim 1, wherein the embolic particles contain a radioisotope, cytotoxic chemotherapy, targeted therapy, antibody, or immunotherapy agent.

15. The computer-implemented method of claim 1, the method further comprising preparing a treatment plan for a patient pursuant to the effective local dose.

16. A computer-implemented method for implementation by one or more data processors, the method comprising:

determining a mean dose of a particle and a particle density at least a portion of tumor and at least a portion of normal tissue;

performing a microdosimetry simulation or calculation, using the mean dose and the particle density;

determining the effective local dose, based on the microdosimetry simulation or calculation; and determining the mean dose and the particle density via a partition model.

17. A system configured to determine an effective local dose for a treatment procedure, the system comprising:

a non-transitory computer readable medium comprising instructions executable by a processor to cause the processor to:

determine a mean dose of a particle and a particle density at least a portion of tumor and at least a portion of normal tissue;

perform a microdosimetry simulation or calculation, using the mean dose and the particle density;

determine the effective local dose, based on the microdosimetry simulation or calculation; and determining the mean dose and the particle density via a partition model.

18. A method of determining an effective local dose for a treatment procedure, comprising:

determining a mean dose of a particle and a particle density at least a portion of tumor and at least a portion of normal tissue;

performing a microdosimetry simulation or calculation, using the mean dose and the particle density; and determining the effective local dose, based on the microdosimetry simulation or calculation;

using a formula $$g\left(1+\frac{a}{d}+\frac{b}{\sqrt[3]{d}}\right)^{-c}$$

to calculate the effective local dose, where g is a mean dose, d is a particle density, and wherein a=36.5, b=3.42 and c=2, and wherein a continuous function is used to approximate the microdosimetry simulation.

* * * * *